(12) United States Patent
Egolf et al.

(10) Patent No.: US 7,350,971 B2
(45) Date of Patent: Apr. 1, 2008

(54) METHOD AND DEVICE FOR MEASURING THE THERMAL CONDUCTIVITY OF A MULTIFUNCTIONAL FLUID

(75) Inventors: Peter Williams Egolf, Niederlenz (CH); Osmann Sari, Prilly (CH)

(73) Assignee: Haute Ecole d'Ingénierie et de Gestion du Canton de Vaud, Yverdon-Les-Bains (CH)

( * ) Notice: Subject to any disclaimer, the term of this patent is extended or adjusted under 35 U.S.C. 154(b) by 0 days.

(21) Appl. No.: 10/536,855

(22) PCT Filed: Nov. 28, 2003

(86) PCT No.: PCT/CH03/00788

§ 371 (c)(1),
(2), (4) Date: Jul. 26, 2005

(87) PCT Pub. No.: WO2004/048953

PCT Pub. Date: Jun. 10, 2004

(65) Prior Publication Data

US 2006/0062273 A1    Mar. 23, 2006

(30) Foreign Application Priority Data

Nov. 28, 2002   (CH) .................................. 2007/02

(51) Int. Cl.
*G01N 25/18* (2006.01)
*G01K 3/00* (2006.01)
*G01K 13/00* (2006.01)

(52) U.S. Cl. .................. 374/44; 374/110; 374/102; 374/148

(58) Field of Classification Search .............. 374/43, 374/44, 101, 102, 29, 30, 110, 166
See application file for complete search history.

(56) References Cited

U.S. PATENT DOCUMENTS 5,232,543 A * 8/1993 Frelich et al. .............. 156/497
5,258,929 A * 11/1993 Tsuchida ..................... 702/136
5,311,447 A * 5/1994 Bonne ......................... 702/50

FOREIGN PATENT DOCUMENTS

DE    199 49 327 A    4/2001

OTHER PUBLICATIONS

Parker W J et al: "Flash Method of Determining Thermal Diffusivity, Heat Capacity, and Thermal Conductivity" Journal of Applied Physics, American Institute of Physics, New York, US, vol. 32, No. 9, Sep. 1, 1961, pp. 1679-1684, XP000616804 ISSN: 0021-8979 Article de base sur le principe de la mesure par "flash laser" the whole document.

(Continued)

*Primary Examiner*—Gail Verbitsky
*Assistant Examiner*—Mirellys Jagan
(74) *Attorney, Agent, or Firm*—Davis Bujold & Daniels, P.L.L.C.

(57) ABSTRACT

The invention relates to a method and a device for the continuous measurement (30) of the thermal conductivity of a multifunctional fluid. The inventive method consists of: placing a sample of the multifunctional fluid in a space (31) which is defined by an inlet face and an outlet face; transmitting at least one very brief pulse of a heat flux to the sample via the inlet face, using a laser (40); measuring the heat wave at least three points which are spaced out inside the sample; using at least three temperature sensors (S1, S2, S3) in order to determine the change in the temperature of the multifunctional fluid as a function of time at the three spaced-out points inside the sample; deducing the thermodynamic characteristics of the sample from the aforementioned temperature change and calculating the thermal conductivity from equation (I), wherein T represents thermal conductivity which is dependent on temperature, t represents thermal diffusivity which is dependent on k and which is equal to $k(T)/\rho^*Cp$, $\rho$ and $Cp$ representing mass density and specific heat.

12 Claims, 2 Drawing Sheets

OTHER PUBLICATIONS

Gobbe C et al: "Mise en Oeuvre de la Methode Flashe Pour la Mesure de Diffusivite Thermique Sur Des Materiaux Liquides ou Fondus en Fontcion de la Temperature. Application AUX Polymeres" Revue de Physique Apploquee, Les Editions de Physique. Paris, FR, vol. 24, No. 12, Dec. 1, 1989, pp. 1119-1128, X000080289 p. 1119, col. 1—p. 1120, col. 2 p. 1121, col. 2, paragraph 2.1—p. 1122, col. 2.

Hiromichi Ohta et al: Thermal Diffusivity Measurements of Moten Salts Using a Three-Layered Cell by the Laser Flash Method: Review of Scientific Instruments, American Institute of Physics. New York, US, vol. 61, No. 10, Oct. 1, 1990, pp. 2645-2649, XP000172298 ISSN: 0034-6748 p. 2654, paragraph 1 figure 2.

* cited by examiner

METHOD AND DEVICE FOR MEASURING THE THERMAL CONDUCTIVITY OF A MULTIFUNCTIONAL FLUID

This application is a national stage completion of PCT/CH2003/000788 filed Nov. 28, 2003 which claims priority from Swiss Application Ser. No. 2007/02 filed Nov. 28, 2002.

FIELD OF THE INVENTION

The present invention concerns a method for the continuous measurement of the thermal conductivity of a multi-functional fluid in which a sample of the multi-functional fluid is passed through a space delimited by a first face, called the entry, and a second face, called the exit, and in which an increase in temperature of the sample of multi-functional fluid is generated and this increase in temperature is measured.

It also concerns a device for the continuous measurement of thermal conductivity of a multi-functional fluid consisting of means for passing a sample of the multi-functional fluid through a space delimited by a first face, called entry, and a second face, called exit, of the sample, means of heating to vary the temperature of this sample and means designed to measure the variation of this temperature.

BACKGROUND OF THE INVENTION

A multi-functional fluid is a fluid which can be comprised of several components which can be in different phases, liquid, solid or gaseous. A simple example of a multi-functional fluid is blood. Other multi-functional fluids are, for example, biphasic mixtures consisting of phase change materials, currently called PCMs, in suspension in a liquid and an ice slurry.

In order to be able to resolve the various problems of heat transfer, fluid flow or other, the numerical values of the physical and thermo-physical properties of fluids are of great importance.

Thermal conductivity in particular defines the degree of propagation of heat in a material as a function of the temperature gradient. Conductivity is essentially a transfer of energy under the effect of movement, notably the vibrations of particles. The coefficient of conductivity k (W/m.K) is dependent on the crystalline structure of solids, on the homogeneity, temperature, pressure, of the liquid, solid or gaseous phases and/or the composition.

It is noted that liquids are better conductors than gases, and solids are better conductors than liquids. The conductivity of liquids depends in the first instance on their temperature.

The precise measurement of the coefficient of conductivity is a difficult operation. In fact, the materials which are presently used are not always similar. This leads to differences in the experimental results established by different research laboratories. Thus, the precision related to the coefficient of conductivity does not exceed 5%.

For simple fluids, without a phase change, methods for the measurement of thermal conductivity already exist.

In order to characterize a multi-functional fluid with or without a change of phase, practically no direct, reliable method of measuring thermal conductivity exists.

The German publication DE 199 49 327 A1 describes a method and a device for the implementation of this method for determining the concentration of a gas in a gaseous mixture comprised of several components. The method is based on the measurement of thermal conductivity of a gaseous mixture which is subjected to an increase in temperature between a minimum and maximum value determined by a temperature/time function. An analysis of the curve of temperature variation as a function of time permits the determination of the concentration of a gas contained in the mixture. The device includes a temperature sensor which transmits a signal to a Fourier analyzer. Such a device is not adapted to the measurement of thermal conductivity of a multi-functional fluid.

SUMMARY OF THE INVENTION

The objective of the present invention is to alleviate this problem by providing a method as well as a device which enables the determination in a rapid, effective and economical manner of the thermodynamic characteristics of a multi-functional fluid, and to deduce the thermal conductivity there from.

This objective is attained by a method as defined in the preamble, and characterized by the facts that:
- through the sample, through the first input face, at least one very brief impulse of heat flux is transmitted,
- the temperature is measured at least three separate points within this sample,
- by means of this measurement, the evolution of the temperature of the multi-functional fluid is measured at these three points as a function of time,
- as a function of this evolution, the thermodynamic characteristics of the sample of the multi-functional fluid is determined, and the thermal conductivity of this sample is determined.

According to one preferred method of implementation, the impulses of heat flux are transmitted in a repetitive manner and a thermogram is established which consists of curves of the temperature evolution as a function of time passing between the sending of a heat flux through the first input face and the increase in temperature determined at the at least three separated points within the sample.

By preference, the thermal conductivity is deduced from the following equation:

$$\frac{\partial T}{\partial t} + \alpha(k)\left[\frac{1}{k} \cdot \frac{dk}{dt}\left(\frac{\partial T}{\partial x}\right)^2 + \frac{\partial^2 T}{\partial x^2}\right] = 0$$

where: T is the temperature
k is the thermal conductivity dependent upon the temperature
t is the time
á is the thermal diffusivity dependant upon k and which is equal to:

$k(T)\rho^*C_p$ with $\rho$ and $C_p$ being the volume mass and the specific heat.

This objective is also attained by the device as defined in the preamble and characterized in that it consists, among other things, of means designed to transmit to the sample, through the first input face, at least a very brief impulse of heat flux, means designed to measure the heat wave at least three separated points within this sample, means designed to determine on the basis of the measured values, the evolution of the temperature of the multi-functional fluid as a function of time at the separated points within the sample, means designed to deduce from this evolution the thermodynamic characteristics of the sample of the multi-functional fluid and means designed to calculate the thermal conductivity of this sample.

According to one preferred method of implementation, the means designed to pass a sample of the multi-functional fluid through the space delimited by the first and second faces includes an enclosure with an insulating lining and an interior coating of polished metal, through which is continually passed the multi-functional fluid.

The means (are) designed to transmit to the sample at least one very brief impulse of heat flux comprised of at least one laser.

According to one particular preferred method of implementation, the means designed to transmit to the sample at least one very brief impulse of heat flux can be comprised of an emitter tube.

The means designed to measure the heat wave which has passed through the sample is comprised preferably of a receiver tube.

According to one particularly advantageous construction, the means designed to determine the evolution of the temperature of the multi-functional fluid as a function of time is comprised of at least three temperature probes designed to measure the temperature of the sample of multi-functional fluid at the at least three points.

The means designed to deduce, from the evolution of the temperature at the three separated points in the sample of the multi-functional fluid, the thermodynamic characteristics of this sample and to calculate its thermal conductivity, preferably comprised of an arithmetic unit designed to receive from the temperature probes signals corresponding to the values measured.

BRIEF DESCRIPTION OF THE DRAWINGS

The present invention and its advantages will become more apparent in the following description of the various modes of implementation of the invention, by making reference to the appended drawings, in which.

DETAILED DESCRIPTION OF THE INVENTION

Figure 1:
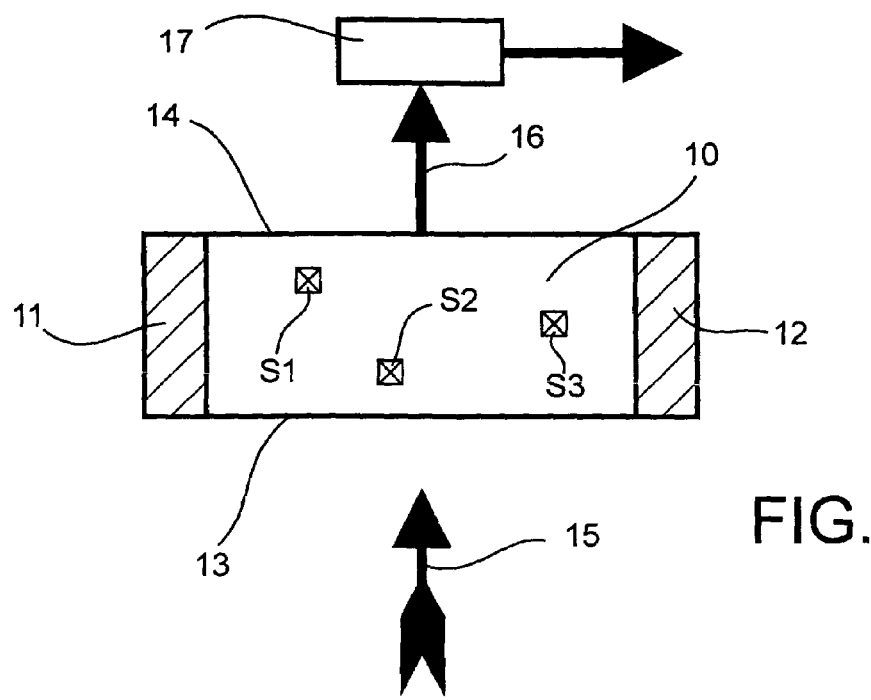
FIG. 1 is a sketch of the principle illustrating the application of the method according to the invention.

With reference to FIG. 1, the method consists firstly of selecting a sample 10 of a multi-functional fluid to be studied, for example, by having it circulate between two linings 11 and 12 which are thermally insulated from a conduit or an enclosure of a form appropriate to define a first face, called input face, 13 and a second face, called exit face, 14. The fluid is preferable subjected to an increase in temperature by conventional means. In addition, at least one very brief impulse of heat flux is transmitted across the first input face 13, illustrated by the arrow 15, for example, by means of a laser. Following this impulse, a heat wave propagates across the sample 10 and crosses the second exit face 14. It is represented by arrow 16 and measured by a device 17. At least three separate probes S1, S2 and S3 within the sample permit the tracing of the temperature evolution curve of the multi-functional fluid as a function of time by providing a thermogram. An arithmetic unit enables the deduction from this evolution of the thermodynamic characteristics of the sample of the multi-functional fluid, and the calculation of the thermal conductivity of this sample. The method preferably includes the repeated emission of heat flashes and the measurement is conducted in a repetitive manner.

Figure 2:
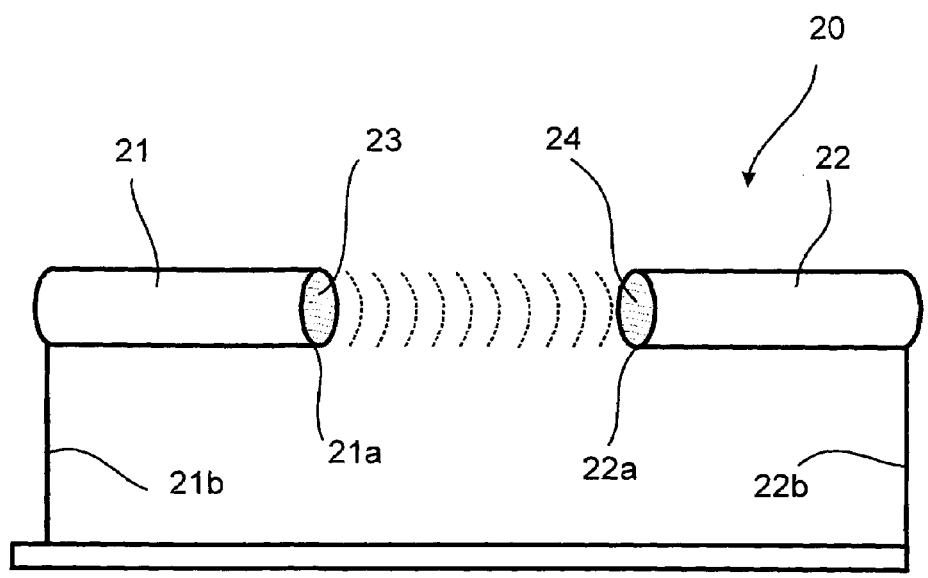
FIG. 2 is a view illustrating schematically a mode of implementation of the invention device.

Device 20 for the implementation of the method of measuring the thermal conductivity of a sample of a multi-functional fluid, illustrated by way of a non-limiting example, in the form of an advantageous implementation by FIG. 2, consists of a first emitter tube 21 and a second receiver tube 22, set up in such a way that the space separating their respective extremities 21a and 22a define the first input face 23 and the second output face 24 of this sample. An impulse, called a flash of heat flux, is emitted by the emitter tube 21, crosses the sample in the form of a heat wave and is captured by the receiver tube 22. The two tubes are advantageously several centimeters in length and have a diameter of less than 0.01 m. They contain the electronic components required to control the impulses and manage the measurements. They are mounted respectively on two supports 21b and 22b comprised of rigid conducting wires.

Figure 3:
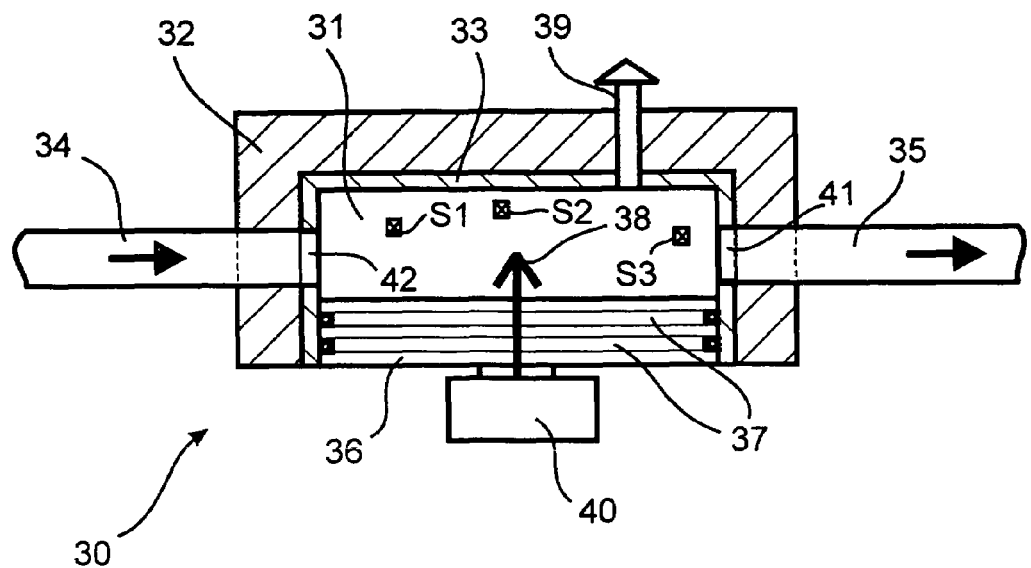
FIG. 3 is a section view of an advantageous mode of implementation of the invention device.

FIG. 3 is a cross sectional view of a measuring device 30 according to the invention. It is mainly comprised of an enclosure 31 with an insulating lining 32 and an interior coating of polished metal 33. This enclosure is traversed continually by a multifunctional fluid, such as for example an ice slurry for which we wish to know the thermal conductivity. This fluid enters enclosure 31 by means of a conduit 34 and leaves this enclosure by a conduit 35. It is in addition equipped with a chamber 36 containing heating elements 37 which are designed to vary the temperature of the sample of multi-functional fluid. In addition, impulses of heat flux, represented by an arrow 38, are generated preferably in a repetitive manner, across the input face, for example, by a laser 40. The heat waves generated traverse the sample of fluid contained in the enclosure 31, exiting from the enclosure (arrow 39) and are measured by at least three temperature probes S1, S2 and S3 separated from one another and located within the sample. The thickness e of the enclosure 31 is known precisely. This thickness can be variable to enable variation of the measurement parameters. To this end, device 30 is equipped with instrumentation (not shown) comprised of a micrometer which allows the precise determination of the thickness e of the enclosure 31. The two conduits 34 and 35 are respectively equipped with a valve 41, 42 which allows continuous control of the input, exit and circulation of the multi-functional fluid in the enclosure.

Figure 4:
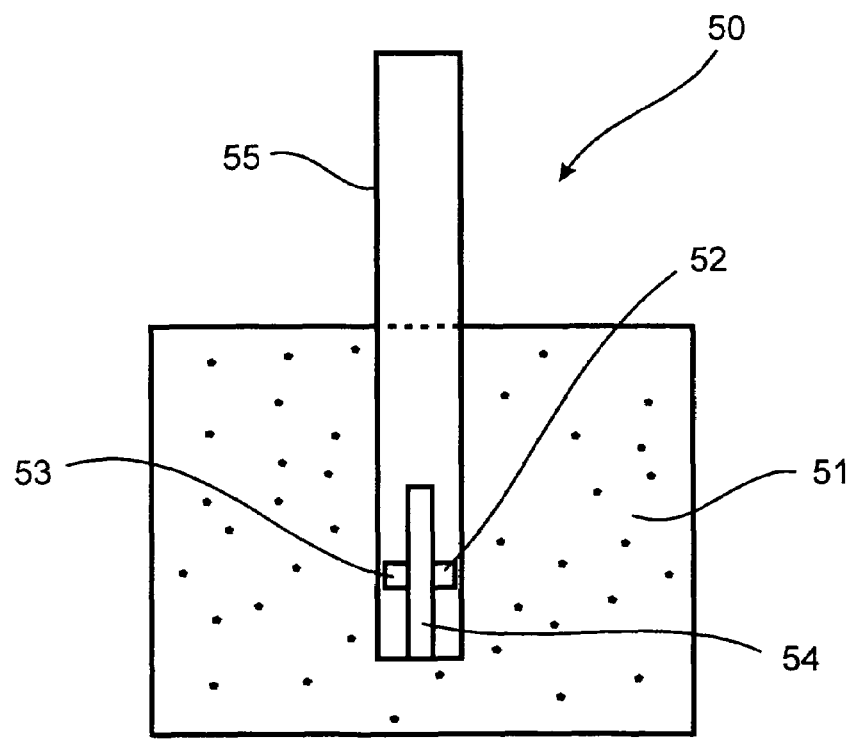
FIG. 4 represents a cross sectional view of a measuring probe used in the invention device.

The probe 50, schematically represented by FIG. 4, corresponds to an advantageous form of implementation of the temperature probes S1, S2 and S3 mentioned above. In fact, it combines the measurement of the temperature and the measurement of the electrical conductivity. It is immersed in the multi-functional fluid 51. It is comprised of a temperature sensor 52 and an electrical conductivity measurement sensor 53 of the multi-functional fluid. These two sensors are for example, mounted on the interior lining of a tubular element 54 carried by a support 55 which is immersed in the multi-functional fluid.

The device according to the invention functions advantageously in the following manner. The means, for example the enclosure 31, permits the insulation of a sample of the multi-functional fluid. The means, consisting of, example, instrumentation comprising a micrometer, enables the determination of the thickness of the enclosure. The means, for example, consisting of heating elements 37, enabling the generation and raising of the sample temperature. The means such as the laser 40 enabling the generation and transmission through the sample of at least one very brief impulse of heat flux and preferably, a series of such impulses. The means such as the receiver tube 22, illustrated in FIG. 2, enabling the measurement of the heat wave which has traversed the sample. The temperature sensor 52 of FIG. 4 allows the determination of the temperature evolution of the multi-functional fluid as a function of time. An arithmetic unit (not shown) enables the deduction from this evolution of the thermodynamic characteristics of the sample of the fluid, and the calculation of the thermal conductivity of this sample.

To determine the thermal conductivity, it is advisable to solve the heat equation by considering that thermal conductivity is a function which is dependent on the temperature. This equation is the following:

$$\frac{\partial T}{\partial t} + \alpha(k)\left[\frac{1}{k} \cdot \frac{dk}{dT}\left(\frac{\partial T}{\partial x}\right)^2 + \frac{\partial^2 T}{\partial x^2}\right] = 0$$

where: T is the temperature k is the thermal conductivity dependent on the temperature t is the time á is the thermal diffusivity dependent on k, and equals:

k(T)/ρ*Cp with ρ and Cp the volume mass and the specific heat.

By discretising this equation with the help of appropriate software and by using the values for thermal conductivity given by a model called the Jeffrey model, a family of curves is obtained which constitute a thermogram.

The thermal conductivity can be determined by using the thermogram which is constituted on the basis of the only experimental data available. In this regard, it is advisable to rewrite the heat equation by bringing out two temperature dependant coefficients:

$$\frac{\partial T}{\partial t} = a\frac{\partial^2 T}{\partial x^2} + b\left(\frac{\partial T}{\partial x}\right)^2$$

in which:

$$a = \frac{k}{\rho C_F}, b = \frac{1}{k} \cdot \frac{dk}{dT} a$$

By writing this equation twice for two very close locations, the first at the point x and the second at the point x+dx, a system of two equations in two unknowns is obtained. It is assumed that the coefficients a and b at points x and x+dx are equal. By putting this system into matrix form, it can be solved very simply by means of appropriate software, and the thermal conductivity of the sample can be found.

The phase change materials currently called PCMs (Phase Change Material) are alkane polymers with a solid-liquid phase change temperature varying between 0 and 65° C. The PCMs offer an advantage for static uses, for example, storage, and dynamic uses, for example, the transport of thermal energy.

The addition of microcapsules (10 μm to 1,000 μm) of PCM materials such as for example, naphthalene in the solid phase in a liquid in suspension gives a biphasic mixture in liquid form currently called <<PCMS>> which can be put into circulation by use of conventional methods, for example, a pump. This aqueous solution allows the combining in an ecological and economical manner of the advantages of storage and distribution of energy in the form of heat and cold, and of indirect systems.

Such a PCMS is constituted by the ice slurry. The addition of small grains or flakes of ice into an aqueous solution yields a mixture in the liquid form which can be pumped. This mixture offers the possibility of combining in an ecological and economical manner the advantages of storing of cold and of indirect cooling with the high power refrigerating of direct expansion.

With respect to probe 50 in particular, other methods of construction can be envisaged. The sensors for temperature and the measurement of a conductivity are available on the market. Their arrangement on an immersion support in the multi-functional fluid could be adapted as a function of requirements and applications.

The invention claimed is:

1. A method for continuous measurement of thermal conductivity of a multi-functional fluid, the method comprising the steps of:
    passing a sample of the multi-functional fluid through a space delimited by a first input face and a second exit face;
    generating an increase in temperature of the sample of multi-functional fluid, at least by a very brief impulse of heat flux transmitted to the sample, through the first input face;
    measuring the temperature increase in at least three separated points within the sample;
    determining with the temperature increase measurement, an evolution of the multi-functional fluid temperature at the three points as a function of time;
    determining thermodynamic characteristics of the sample of the multi-functional fluid as a function of the evolution; and
    calculating a thermal conductivity of the sample based on the determined evolution.

2. The method according to claim 1, further comprising the step of transmitting the impulses of heat flux in a repetitive manner; and
    establishing a thermogram consisting of temperature evolution curves as a function of an amount of time between the transmitting the impulses of heat flux through the first input face and the evolution of temperature as determined at the three separated points within the sample.

3. The method according to claim 1, further comprising the step of deducing the thermal conductivity with the following equation:

$$\frac{\partial T}{\partial t} + \alpha(k)\left[\frac{1}{k} \cdot \frac{dk}{dT}\left(\frac{\partial T}{\partial x}\right)^2 + \frac{\partial^2 T}{\partial x^2}\right] = 0$$

where: T is the temperature;
    k is the thermal conductivity dependent upon the temperature;
    t is the time;
    α is the thermal diffusivity dependant upon k and which is equal to:

k(T)/ρ-Cp with ρ and Cp being the volume mass and the specific heat and where x is the relative location of one of the three points.

4. A device for continuous measurement of thermal conductivity of a multi-functional fluid, the device comprising;
    a means designed to pass a sample of the multi-functional fluid through a space delimited by a first input face and a second exit face of the sample;

a means for heating the sample to vary a temperature of the sample, a means to measure variation of the temperature of the sample a means to transmit to the sample, at least a very brief impulse of heat flux, through the first input face, a means to measure a heat wave at three or more separate points within the sample;

a means to determine, on a basis of values measured, a temperature evolution of the multi-functional fluid as a function of time at the separate points within the sample;

a means to deduce, from the temperature evolution, thermodynamic characteristics of the sample of the multi-functional fluid; and a means to calculate thermal conductivity of this sample, and;

wherein the means to determine the temperature evolution of the multi-functional fluid as a function of time comprises at least three temperature probes (S1, S2, S3) designed to measure the temperature of the sample of the multi-functional fluid at the at least three separated points within the sample.

5. The device according to claim 4, wherein the means to pass the sample of the multi-functional fluid through the space delimited by the first and second faces includes an enclosure (31) with an insulating lining (32) and an interior coating of polished metal (33), which is continuously traversed by the multi-functional fluid.

6. The device according to claim 4, wherein the means (37) to transmit the at least one very brief impulse of the heat flux comprises at least one laser 40).

7. Device according to claim 4, wherein the means to transmit the at least one very brief impulse of the heat flux comprises an emitter tube (21).

8. The device according to claim 4, wherein the means to measure the heat wave which has traversed the sample comprises a receiver tube (22).

9. The device according to claim 4, wherein the means to deduce from the temperature evolution at the three separate points in the sample of multi-functional fluid, the thermodynamic characteristics of the sample and to calculate the thermal conductivity comprises an arithmetic unit designed to receive from the temperature probes, the signals corresponding to the values measured.

10. A method for continuous measurement of thermal conductivity of a multi-functional fluid, the method comprising the steps of:

passing a sample of the multi-functional fluid through a space delimited by a first input face and a second exit face;

generating an increase in temperature of the sample of multi-functional fluid, at least by a very brief impulse of heat flux transmitted to the sample, through the first input face;

measuring the temperature increase with at least three temperature probes within the sample;

determining with the temperature increase measurement, an evolution of the multi-functional fluid temperature at the three temperature probes as a function of time;

determining thermodynamic characteristics of the sample of the multi-functional fluid as a function of the evolution; and calculating a thermal conductivity of the sample.

11. The method according to claim 10, further comprising the step of transmitting the impulses of heat flux in a repetitive manner; and establishing a thermogram consisting of temperature evolution curves as a function of an amount of time between the transmitting the impulses of heat flux through the first input face and the evolution of temperature as determined at the three separated points within the sample.

12. The method according to claim 10, further comprising the step of deducing the thermal conductivity with the following equation:

$$\frac{\partial T}{\partial t} + \alpha(k)\left[\frac{1}{k} \cdot \frac{dk}{dt}\left(\frac{\partial T}{\partial x}\right)^2 + \frac{\partial^2 T}{\partial x^2}\right] = 0$$

where: T is the temperature;

k is the thermal conductivity dependent upon the temperature;

t is the time;

$\alpha$ is the thermal diffusivity dependant upon k and which is equal to:

k(T)/$\rho$-Cp with $\rho$ and Cp being the volume mass and the specific heat and where x is the relative location of one of the three separated points.

* * * * *